United States Patent
Frielinghaus et al.

(10) Patent No.: US 11,759,261 B2
(45) Date of Patent: *Sep. 19, 2023

(54) AUGMENTED REALITY PRE-REGISTRATION

(71) Applicant: Brainlab AG, Munich (DE)

(72) Inventors: Nils Frielinghaus, Heimstetten (DE); Christoffer Hamilton, Aschheim (DE)

(73) Assignee: BRAINLAB AG, Munich (DE)

(*) Notice: Subject to any disclaimer, the term of this patent is extended or adjusted under 35 U.S.C. 154(b) by 27 days.

This patent is subject to a terminal disclaimer.

(21) Appl. No.: 17/487,464

(22) Filed: Sep. 28, 2021

(65) Prior Publication Data
US 2022/0008135 A1 Jan. 13, 2022

Related U.S. Application Data

(63) Continuation of application No. 16/488,152, filed as application No. PCT/EP2017/055691 on Mar. 10, 2017, now Pat. No. 11,135,016.

(51) Int. Cl.
*A61B 34/10* (2016.01)
*G06F 3/01* (2006.01)
(Continued)

(52) U.S. Cl.
CPC .............. *A61B 34/10* (2016.02); *G06F 3/011* (2013.01); *G06V 20/20* (2022.01);
(Continued)

(58) Field of Classification Search
CPC .............. A61B 34/10; A61B 2034/107; A61B 2034/2055; A61B 2090/365;
(Continued)

(56) References Cited

U.S. PATENT DOCUMENTS

| D440,241 S | 4/2001 | Kawahara et al. |
| D613,781 S | 4/2010 | Liu et al. |

(Continued)

FOREIGN PATENT DOCUMENTS

| WO | 2005088539 | 9/2005 |
| WO | 20120642482 | 5/2012 |

(Continued)

OTHER PUBLICATIONS

International Search Report and Written Opinion for PCT Application No. PCT/EP2017/055691 dated Oct. 10, 2017.

*Primary Examiner* — Maurice L. McDowell, Jr.
(74) *Attorney, Agent, or Firm* — Gray Ice Higdon

(57) ABSTRACT

The disclosed method encompasses pre-registering an anatomical body part with a coordinate system used by an augmented reality device (such as augmented reality glasses) for outputting (e.g. displaying or projecting) augmentation information. An example of the augmentation information is the position (in the real image captured by the augmented reality device) of a fine registration area on the anatomical body part which a user is supposed to identify for fine registration of the anatomical body part with a tracking coordinate system used by a medical position tracking system. The disclosed method is usable in a medical environment such as for surgery or radiotherapy.

17 Claims, 8 Drawing Sheets

(51) Int. Cl.
*G06V 20/20* (2022.01)
*A61B 34/20* (2016.01)
*A61B 90/00* (2016.01)

(52) U.S. Cl.
CPC . *A61B 2034/107* (2016.02); *A61B 2034/2055* (2016.02); *A61B 2090/365* (2016.02); *A61B 2090/3937* (2016.02)

(58) Field of Classification Search
CPC .... A61B 2090/3937; A61B 2034/2051; G06F 3/011; G06V 20/20; G16H 40/63; G16H 20/40; G06T 3/0068; G06T 7/30
See application file for complete search history.

(56) References Cited

U.S. PATENT DOCUMENTS

| | | |
|---|---|---|
| D624,104 S | 9/2010 | Miyake et al. |
| D650,820 S | 12/2011 | Long |
| D677,294 S | 3/2013 | Long |
| D678,378 S | 3/2013 | Selic |
| D755,268 S | 5/2016 | Parrot |
| D766,348 S | 9/2016 | Long |
| D769,343 S | 10/2016 | Bordegnoni et al. |
| 11,135,016 B2 * | 10/2021 | Frielinghaus .......... G06V 20/20 |
| 2003/0210812 A1 * | 11/2003 | Khamene ............... A61B 90/36 382/128 |
| 2004/0002642 A1 * | 1/2004 | Dekel ..................... G06T 7/74 600/407 |
| 2005/0215879 A1 | 9/2005 | Chuanggui |
| 2007/0018975 A1 | 1/2007 | Chuanggui et al. |
| 2008/0123910 A1 | 5/2008 | Zhu |
| 2012/0109151 A1 | 5/2012 | Maier-hein et al. |
| 2012/0120070 A1 * | 5/2012 | Baillot .................. G08B 25/14 345/419 |
| 2013/0245461 A1 | 9/2013 | Maier-hein et al. |
| 2013/0267838 A1 * | 10/2013 | Frank ..................... A61B 5/064 600/424 |
| 2013/0293578 A1 | 11/2013 | Leung |
| 2014/0135746 A1 * | 5/2014 | Schoepp ............... A61B 5/061 606/1 |
| 2014/0275760 A1 | 9/2014 | Lee et al. |
| 2015/0246449 A1 | 9/2015 | Sakai et al. |
| 2016/0000515 A1 * | 1/2016 | Sela ....................... G06T 7/248 600/424 |
| 2016/0191887 A1 | 6/2016 | Casas |
| 2016/0324580 A1 | 11/2016 | Esterberg |
| 2018/0012416 A1 * | 1/2018 | Jones .................... G06F 3/0346 |
| 2018/0168740 A1 * | 6/2018 | Ryan ..................... A61B 90/36 |
| 2018/0303558 A1 | 10/2018 | Thomas |
| 2018/0317803 A1 | 11/2018 | Ben-yishai et al. |
| 2020/0078100 A1 | 3/2020 | Weinstein et al. |
| 2020/0138518 A1 | 5/2020 | Lang |

FOREIGN PATENT DOCUMENTS

| | | |
|---|---|---|
| WO | 2015164402 | 10/2015 |
| WO | 2016162789 | 10/2016 |
| WO | 2018162079 | 9/2018 |

* cited by examiner

AUGMENTED REALITY PRE-REGISTRATION

The present invention relates to a computer-implemented medical method for pre-registering an anatomical body part of a patient's body, using the output of an augmented reality device having a distance measurement unit. The invention also relates to a computer configured to execute a program corresponding to the method and a medical system for pre-registering an anatomical body part of a patient's body, using the output of an augmented reality device having a distance measurement unit, the medical system comprising a computer of the aforementioned kind.

TECHNICAL BACKGROUND

Using an augmented reality device with depth sensors in combination with surgical or radiotherapy tracking devices enables the combined information to be used to display augmented information regarding the surgical navigation or radiotherapy tracking inside the augmented reality device. This can be used to optimize the steps required to complete a surgical navigation registration, including removing, replacing or quickening currently performed steps with e.g. optical or electromagnetic surgical navigation.

There is currently no equivalent to this. So far, augmented reality devices have been demonstrated in surgical navigation to overlay patient anatomy renderings over real patient anatomy. The information that we suggest to display in the augmented devices is currently usually displayed on the navigation system computer screen.

Registration in surgical navigation is today performed according to well-established methods, generally using instruments to define a spatial relationship between patient anatomy and objects tracked by the tracking system.

The present invention is designed to provide a method for pre-registering an anatomical body part of a patient's body which offers improved user guidance.

Aspects of the present invention, examples and exemplary steps and their embodiments are disclosed in the following. Different exemplary features of the invention can be combined in accordance with the invention wherever technically expedient and feasible.

Exemplary Short Description of the Present Invention

In the following, a short description of the specific features of the present invention is given which shall not be understood to limit the invention only to the features or a combination of the features described in this section.

The disclosed method encompasses pre-registering an anatomical body part with a coordinate system used by an augmented reality device (such as augmented reality glasses) for outputting (e.g. displaying or projecting) augmentation information. An example of the augmentation information is the position (in the real image captured by the augmented reality device) of a fine registration area on the anatomical body part which a user is supposed to identify for fine registration of the anatomical body part with a tracking coordinate system used by a medical position tracking system. The disclosed method is usable in a medical environment such as for surgery or radiotherapy.

General Description of the Present Invention

In this section, a description of the general features of the present invention is given for example by referring to possible embodiments of the invention.

In general, the invention reaches the aforementioned object by providing, in a first aspect, a computer-implemented medical method for pre-registering an anatomical body part of a patient's body, using the output of an augmented reality device having a distance measurement unit.

Augmented reality (AR) is a live direct or indirect view of a physical, real-world environment whose elements are augmented (or supplemented) by computer-generated sensory input such as sound, video, graphics or GPS data.

The method according to the first aspect is for example a data processing method. The method according to the first aspect comprises executing, on at least one processor of at least one computer (for example at least one computer being part of a position tracking system), the following exemplary steps which are executed by the at least one processor.

In a (for example first) exemplary step, a pre-registration of the anatomical body part with an augmented reality coordinate system associated with the augmented reality device is determined based on the result of a distance measurement by the distance measurement unit. The augmented reality coordinate system is a coordinate system in which positions of objects imaged by the augmented reality device are defined and in which positional values (coordinates) of augmentation information are defined for display by the display of the augmented reality device. Within the meaning of this disclosure, the pre-registration is understood to be a relative position between the position of the anatomical body part and the augmented reality coordinate system. In other words, the pre-registration delivers information about and/or constitutes the position of the anatomical body part in the augmented reality coordinate system.

For example, the display of the augmented reality device comprises a head-mounted display (a head-mounted display unit). Specifically, the display of the augmented reality device may be included in glasses (eyeglasses) wearable by a user. A head-mounted display (HMD) is a display device paired to the forehead such as a harness or helmet. The HMD places an image of both the physical world and virtual objects over the user's field of view. The HMD may employ sensors for six degrees of freedom monitoring that allow the system to align virtual information (the augmentation information) to the physical world and adjust accordingly with the user's head movements. Alternatively, the display of the augmented reality device can be rendered on a device resembling eyeglasses. Versions include eyewear that employ cameras to intercept the real world view and re-display its augmented view through the eye piece and devices in which the AR imagery is projected through or reflected off the surfaces of the eyewear lens pieces. Alternatively, the augmented reality device may be embodied by a head-up display which can show data, information, and images while the user views the real world.

The augmented reality device is for example configured to display visual information on its display, for example to display the visual information as an overlay to a real image acquired with the augmented reality device. A real image is understood to be an image describing the physical scene in the field of view of the augmented reality device. To that end, the augmented reality device comprises an output unit such as a display (display unit) or a projector unit. The display of the augmented reality device may be an entirely digital display (for example, a monitor or a screen upon which a digital image is projected), or an optical display, for example a transparent (e.g. glass or plastic) screen which is transparent for a user to view the real image and may additionally serve as a projection screen for projecting digitally generated information onto, for example as augmentation information for augmenting the information content of the real image. The augmentation information may thus be displayed as an overlay on the real image. Alternatively, the real image may be acquired digitally and rendered on a digital display of the augmented reality device, and the augmentation information may be displayed together (for example, simultaneously) with the digitally rendered real image.

The augmented reality device comprises a distance measurement unit for measuring a distance (also called depth) between the augmented reality device and a specific object which is for example located in the field of view of the augmented reality device. The distance is defined for example as a vector in two or three dimensions. The distance measurement unit for example functions on the principle of measuring distance by detecting light reflections of measurement light from a surface of a real object to at least one light sensor included in the augmented reality device. For example, the distance measurement unit has at least one detecting unit (such as a CCD sensor) for detecting reflections of the measurement light from the physical object. Additionally, the distance measurement unit may have at least one light source for emitting measurement light onto the physical object. Alternatively, or additionally, the measurement light may be emitted by an external light source which is not part auf the augmented reality device. The measurement light may be in the visible or infrared wavelength range. The distance is measured based on the principle of triangulation (using for example two stereoscopic detecting units) or time-of-flight (using for example at least one—for example only one—detecting unit).

In a further (for example second) exemplary step, the position of a fine registration region (being an area or at least one point, for example single point or a plurality of spatially separated [spaced apart] points) of the anatomical body part in a real image (i.e. an image of the real world, i.e. the scene lying in the field of view of the augmented reality device) acquired by the augmented reality device is determined based on the pre-registration. The fine registration region is an area which shall serve as a detected area for fine (e.g. full) registration of the anatomical body part (specifically, the position of the anatomical body part) with a tracking coordinate system of a medical position tracking system. The fine registration can be effected for example by using a pointing tool tracked (detected) by the position tracking system for identifying at least one point in the fine registration region to the position tracking system, and to thereby define the position at which the pointing tool is pointed in the tracking coordinate system. The position of the fine registration region is available for example from a pre-defined data set acquired by the disclosed method and describing the usual position of the fine registration region for the (specific) anatomical body part. The position described by the pre-defined data set is transformed into the augmented reality coordinate system by applying the pre-registration of the anatomical body part to the position described by the pre-defined data set. Thereby, the position of the fine registration region is determined in the augmented reality coordinate system and can be accordingly displayed as augmentation information in the display of the augmented reality device. The pre-defined data set defining the fine registration region is in one example available as a defined region of an anatomical body stored in an anatomical atlas (e.g. atlas data), e.g. the forehead is defined as a region in the anatomical atlas. Alternatively, the pre-defined data set in one example may be determined by evaluating characteristics of medical image data of the patient such as e.g. regions representing a strong curvature or regions that are accessible from a certain direction.

In a (for example third) exemplary step, augmentation information describing the position of the fine registration region is displayed on the display of the augmented reality device. The augmentation information is for example visual information which is output by the output unit of the augmented reality device, for example graphically output (displayed) on the display of the augmented reality device or projected (for example, as optical information) by the augmented reality device (e.g. by a projector unit included in the augmented reality device) into an eye of a user (e.g. a user of the augmented reality device). The augmentation information is determined based on the position of the fine registration region and is displayed for example simultaneously with the real image acquired by the augmented reality device. In an example, the augmentation information is displayed as an overlay onto the real image.

In examples, the augmentation information describes (for example, further describes) at least one of the following:

at least one surface area or at least one point on the anatomical body part which has to be positionally identified for the fine registration;

at least one surface area or at least one point on the anatomical body part which has to be positionally identified for the fine registration but is not within the field of view of a medical position tracking system usable to conduct the fine registration;

at least one part of the fine registration region which has already been identified to a medical position tracking system, for example by using a pointing device, for example a handheld pointing device, for conducting the fine registration;

at least one visual indication (e.g. a text label or colouring, i.e. coloured encoding, or isolines defined in two or three spatial dimensions) describing a region (i.e. at least one of an area or volume) associated with a determined accuracy of the positional tracking by a medical position tracking system (i.e. indicating how accurate surgical navigation would be at specific positions in the augmented reality coordinate system);

at least one instruction to a user how to apply a previously selected method for conducting the fine registration;

at least one region (i.e. at least one of area or volume) which shall (i.e. at least one of must or should) not be positionally identified for the fine registration (for example, the position of a ventilation tube fixed to the patient should be avoided to avoid disturbance of the ventilation process and/or because it is not found in the pre-operative data and may be identified by comparing a planning image describing the patient's face but not including a representation of the ventilation tube to the real image, and determining any difference between the two images).

For example, the augmentation information has been customized for a user of the augmented reality device, for example a subset of available augmentation information is displayed in the augmentation device and where the definition of the subset is determined by a user profile. The customization may encompass determining a role of the user in a medical environment such as an operating room, for example whether the user is an operating surgeon or an assistant such as a nurse or junior surgeon. Accordingly, information may be selected as augmentation information for the user as required by his role. For example, an assistant as a user may be displayed a warning to stand clear of the fine registration region so as to avoid any collision with the fine registration procedure, while the operating surgeon may be displayed guidance information how to use a pointing device for effecting the fine registration.

In one example, of the method according to the first aspect, the pre-registration is to be used for comparison with the full registration, for example to determine the quality of the full registration. To this end, a marker device may be placed (for example, on the patient's body) in a predetermined (i.e. at least one of known or fixed) spatial relationship (i.e. at least one of position or orientation) to the anatomical body part (specifically, to the position of the anatomical body part). The marker device may be tracked by the tracking system and identified in the real image captured by the augmented reality device. By positionally registering a viewing direction of the augmented reality device with the tracking coordinate system to generate an augmented reality device registration, the pre-registration may be compared to the full registration by comparing for example the respectively determined position of the marker device and/or the anatomical body part to one another to determine any potential deviation between the two determined positions. Furthermore, the augmented reality device registration may serve as a basis for determining at least one of the pre-registration or the position of the fine registration region.

The augmented reality device registration may be generated according to at least one of the following examples 1 to 7 for positionally registering the augmented reality device with the tracking coordinate system:

Example 1 for Positionally Registering the Augmented Reality Device with the Tracking Coordinate System In this example, the object is at least a physical object and the position tracking system in this example is an infra-red tracking system and an infrared-reflective marker device is attached to the physical object in a predetermined (at least one of known or fixed) position relative to the physical object for allowing tracking of the physical object by the position tracking system. Alternatively, the position tracking system is an electromagnetic tracking system and an electromagnetic marker device (an array of resonator coils) is attached to the physical object in a predetermined (at least one of known or fixed) position relative to the physical object for allowing tracking of the physical object by the position tracking system. The (infrared-reflective or electromagnetic) marker device is then tracked by the position tracking system, for example by emitting infrared light onto the infrared-reflective marker device or by emitting electromagnetic waves in the resonance range of the array of resonator coils onto the electromagnetic marker device, and detecting the signal returned from the respective marker device in space, for example using a multi-dimensional positional detector such as an infrared-sensitive stereoscopic camera or an array of electromagnetic detection circuits.

In this example, the method may comprise for example the following steps:

marker device template data is acquired (for example, from constructional data of the marker device such as computer-aided design data) which describes a geometrical template of the marker device (e.g. a geometrical configuration of the marker device defined by the constructional data);

surface detection data which describes a surface geometry of the marker device is acquired based on a distance measurement by the distance measurement unit of the augmented reality device (for example, the distance measurement unit is used to scan the surface of the marker device, and a surface model of the marker device is generated based on the scanned surface points on the surface of the marker device according to their respectively determined distance from the augmented reality device);

a relative position between the augmented reality device and the marker device is determined based on the surface detection data and the marker device template data (for example, by comparing the surface appearance of the marker device according to the surface detection data and the marker device template data, respectively, taking into account the determined distance between the marker device and the augmented reality device and/or the distance measurement unit);

the viewing direction of the augmented reality device is positionally registered with the position tracking coordinate system based on the determined relative position between the augmented reality device and the marker device. For example, the augmented reality device registration is then determined based on the distance between the augmented reality device and the marker device and the position of the marker device tracked (determined) by the position tracking system according to known operations of linear algebra.

Example 2 for Positionally Registering the Augmented Reality Device with the Tracking Coordinate System In this example, a physical object (for example, the marker device or the anatomical body part) is captured in the real image, and the method comprises the following steps:

physical object template data is acquired which describes a geometrical template of the physical object;

surface detection data which describes a surface geometry of the physical object is acquired based on a distance measurement by the distance measurement unit (for example, the distance measurement unit of the augmented reality device is used to scan the surface of the physical object, and a surface model of the physical object is generated based on the scanned surface points on the surface of the physical object according to their respectively determined distance from the augmented reality device);

a relative position between the augmented reality device and the physical object is determined based on the surface detection data and the physical object template data (for example, by comparing the surface appearance of the physical object according to the surface detection data and the marker device template data, respectively, taking into account the determined distance between the physical object and the augmented reality device and/or the distance measurement unit);

the viewing direction of the augmented reality device is positionally registered with the tracking coordinate system based on the determined relative position between the augmented reality device and the physical object.

For example, the position of the physical object is tracked by the position tracking system, for example by tracking the position of a marker device attached to the physical object in a predetermined (i.e. at least one of known or fixed) spatial relationship (i.e. at least one of position and orientation) relative to the physical object. For example, the augmented reality device registration is then determined based on the distance between the augmented reality device and the physical object and the position of the physical object tracked (determined) by the position tracking system according to known operations of linear algebra.

If the physical object is anatomical body part, the surface detection data describes a surface geometry of the anatomical body part is acquired based on a distance measurement by the distance measurement unit. The physical object template data is then embodied by anatomical body part template data which describes a geometrical template of at least the surface geometry of the anatomical body part. A relative position between the augmented reality device and the anatomical body part is then determined based on the surface detection data and the anatomical body part template data, and the viewing direction of the augmented reality device is positionally registered with the tracking coordinate system based on the determined relative position between the augmented reality device and the anatomical body part, wherein the pre-registration is determined based on the registration of the viewing direction.

The physical object template data may in this case be acquired from a patient image taken for the specific patient. The patient image is for example a three-dimensional data set taken with a tomographic imaging modality such as computed x-ray tomography or magnetic resonance tomography or ultrasound tomography. Alternatively, or additionally, the physical template data may be acquired from atlas data describing a generic geometrical model of the anatomical body part, or from an individual synthetic template describing a synthesized geometric model of the anatomical body part (which has been generated for example only for the specific patient). Thus, the anatomical body part template data in one example is or has been generated from patient image data describing a medical image of the anatomical body part of the patient's body or in another example from atlas data describing a generic model of at least the surface geometry of the anatomical body part or in an even further example from synthetic template data describing a synthetic template of at least the surface geometry of the anatomical body part.

If the physical object is a device such as a medical device (e.g. an instrument or a patient bed or a marker device or at least a part of the tracking system such as the multi-dimensional position detector, e.g. the stereoscopic camera or array of electromagnetic detection circuits) the physical object template data may be acquired from constructional data such as computer-aided design data of the medical device.

Example 3 for Positionally Registering the Augmented Reality Device with the Tracking Coordinate System In this example, the physical object is also captured in the real image, and the position tracking system has a distance measurement unit (for example working on one of the principles possible for the distance measurement unit of the augmented reality device). In this example, the method comprises the following steps:

surface detection tracking data which describes a surface geometry of the physical object is acquired based on a distance measurement by the distance measurement unit of the tracking system (for example, the distance measurement unit of the tracking system is used to scan the surface of the physical object, and a surface model of the physical object is generated based on the scanned surface points on the surface of the physical object according to their respectively determined distance from the position tracking system and/or the distance measurement unit of the position tracking system);

surface detection data which describes a surface geometry of the physical object is acquired based on a distance measurement by the distance measurement unit of the augmented reality device (for example, the distance measurement unit of the augmented reality device is used to scan the surface of the physical object, and a surface model of the physical object is generated based on the scanned surface points on the surface of the physical object according to their respectively determined distance from the augmented reality device);

the viewing direction of the augmented reality device is positionally registered with the tracking coordinate system
a. based on the surface detection data and the surface detection tracking data and
b. based on the distance measurements by the distance measurement unit of the position tracking system and the distance measurement unit of the augmented reality device.

For example, the surface models of the physical object generated based on the measurements of the distance measurement unit of the augmented reality device and the distance measurement unit of the position tracking system, respectively, are compared using a known algorithm such as the iterative closest point (ICP) or the robust point matching algorithm (RPM), taking into account the distance between the distance measurement unit and the physical object. Thereby, the appearances of the physical object in each of the two surface models can be made comparable, and on the basis of the comparison by searching the scan image output of at least one of the distance measurement units for the model appearance of the physical object in the scan image output of the other one of the two distance measurement units, the position of the physical object can be determined. By knowing the distance between the augmented reality device and the physical object on the one hand and the distance between the position tracking system and/or the distance measurement unit of the position tracking system and the physical object on the other hand, the relative position between the augmented reality device and the position tracking system can be determined so that the position of the augmented reality device in the tracking coordinate system becomes known, thereby generating the augmented reality device registration.

Example 4 for Positionally Registering the Augmented Reality Device with the Tracking Coordinate System In this example, the augmented reality device is tracked by the position tracking system. For example, an infrared-reflective marker device or an electromagnetic marker device is attached to the augmented reality device, for example in a predetermined (i.e. at least one of known or fixed) spatial relationship (i.e. at least one of position or orientation) between the marker device and the viewing direction of the augmented reality device. The viewing direction of the augmented reality device is positionally registered with the tracking coordinate system based on the result of tracking the augmented reality device, for example based on information about the predetermined (i.e. at least one of known or fixed) spatial relationship (i.e. at least one of position or orientation) between the marker device and the viewing direction of the augmented reality device.

Example 5 for Positionally Registering the Augmented Reality Device with the Tracking Coordinate System In this example, the augmented reality device comprises a visible image acquisition unit (e.g. a video or still camera)

for acquiring an image (for example, a digital image) in the visible wavelength range, and wherein the method comprises the following steps:

tracking system surface template data is acquired which describes a geometrical template of at least the surface of at least part of the position tracking system (for example, the multi-dimensional position detector such as the stereotactic camera or array of resonant coil circuits);

an image describing the at least part of the tracking system is obtained from the visible image acquisition unit;

the viewing direction of the augmented reality device is positionally registered with the tracking coordinate system based on the tracking system template data and the image describing the at least part of the position tracking system.

The tracking system surface template data may be acquired from constructional data describing at least the surface geometry of the at least part of the position tracking system, for example computer-aided design data used for constructing the at least part of the position tracking system.

For example, the position of the at least part of the tracking system is determined in the image obtained from the visible image acquisition unit by comparing the surface appearance of the geometrical template of the at least part of the position tracking system with the content of the image obtained from the visible image acquisition unit. The distance between the augmented reality device and the at least part of the position tracking system can be determined by analysing any potential size deviation in the appearance of the at least part of the tracking system in the image compared to its geometrical template.

By knowing the distance between the augmented reality device and the at least part of the tracking system on the one hand and the (predetermined, i.e. at least one of known or fixed) position of the at least part of the position tracking system in the tracking coordinate system on the other hand, the relative position between the augmented reality device and the position tracking system can be determined so that the position of the augmented reality device in the tracking coordinate system becomes known, thereby generating the augmented reality device registration.

Example 6 for Positionally Registering the Augmented Reality Device with the Tracking Coordinate System In this example, the method comprises the following steps:

tracking system surface template data is acquired which describes a geometrical template of at least part of the position tracking system (for example, the multi-dimensional position detector such as the stereotactic camera or array of resonant coil circuits);

tracking system surface detection data is acquired which describes a surface geometry of the at least part of the position tracking system based on a distance measurement by the distance measurement unit of the augmented reality device;

the viewing direction of the augmented reality device is positionally registered with the tracking coordinate system based on the tracking system surface template data and the tracking system surface detection data.

The tracking system surface template data may be acquired from constructional data describing at least the surface geometry of the at least part of the position tracking system, for example computer-aided design data used for constructing the at least part of the position tracking system.

For example, the tracking system surface detection data is acquired based on the output obtained by using the distance measurement unit of the augmented reality device to scan the surface of the at least part of the position tracking system, and a surface model of the physical object. The tracking system surface detection data is generated based on the scanned surface points on the surface of the at least part of the position tracking system according to their respectively determined distance from the augmented reality device).

For example, the position of the at least part of the tracking system is determined in the scan output obtained from the distance measurement unit of the augmented reality device by comparing the surface appearance of the geometrical template of the at least part of the position tracking system with the scan output. The distance between the augmented reality device and the at least part of the position tracking system can be determined by analysing any potential size deviation in the appearance of the at least part of the tracking system in the scan output compared to its geometrical template.

By knowing the distance between the augmented reality device and the at least part of the tracking system on the one hand and the (predetermined, i.e. at least one of known or fixed) position of the at least part of the position tracking system in the tracking coordinate system on the other hand, the relative position between the augmented reality device and the position tracking system can be determined so that the position of the augmented reality device in the tracking coordinate system becomes known, thereby generating the augmented reality device registration.

Example 7 for Positionally Registering the Augmented Reality Device with the Tracking Coordinate System In this example, the augmented reality device comprises a visible image acquisition unit for acquiring an image in the visible wavelength range, and the method comprises the following steps:

code pattern template data is acquired which describes a template of a code pattern attached to at least part of the position tracking system (for example, the multi-dimensional position detector such as the stereotactic camera or array of resonant coil circuits);

a code pattern image describing the code pattern attached to the at least part of the position tracking system is obtained from the visible image acquisition unit;

the viewing direction of the augmented reality device is positionally registered with the tracking coordinate system based on the code pattern template data and code pattern image.

The code pattern may be a visible code such as a bar code or QR (quick response) code, and the augmented reality device or an external computer communicatively coupled to the augmented reality device may be configured to analyze the code pattern image for the information encoded by the code pattern. The code pattern may comprise information for identifying (determining the identity of) the at least part of the tracking system.

The relative position between the augmented reality device and the tracking system is determined by computing the position and orientation of the code pattern relative to the augmented reality device. This is done by iteratively applying linear algebra methods, e.g. the POSIT algorithm (DeMenthon & Davis 1994).

In a further example of the method according to the first aspect, the position tracking system is a structured light tracking system, or comprises an articulable arm positionally registered with the tracking coordinate system.

In a further example of the method according to the first aspect, the position of the fine registration region is determined based on generating a three-dimensional scene using distance measurements by the distance measurement unit of the augmented reality device. The full registration could then be completed without registering the tracking coordinate system with the augmented reality coordinate system. For example, the augmented reality device may identify the anatomical body part and a marker device having a predetermined (i.e. at least one of known or fixed) spatial relationship to the anatomical body part and on that basis display the position of the fine registration region. The fine registration can then be performed in the tracking coordinate system and can be used to connect the two coordinate systems and to gradually/iteratively improve the display of the fine registration region in the display of the augmented reality device.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect.

In a third aspect, the invention is directed to a non-transitory computer-readable program storage medium on which the program according to the second aspect is stored.

In a fourth aspect, the invention is directed to at least one computer (for example, a computer), comprising at least one processor (for example, a processor) and at least one memory (for example, a memory), wherein the program according to the second aspect is running on the processor or is loaded into the memory, or wherein the at least one computer is operably coupled to the program storage medium according to the third aspect for executing the program stored on the program storage medium.

In a fifth aspect, the invention is directed to a (physical, for example electrical, for example technically generated) signal wave, for example a digital signal wave, carrying information which represents the program according to the second aspect.

In a sixth aspect, the invention is directed to a medical system for determining augmentation information relating to positional tracking by a medical position tracking system, the medical system comprising:

the at least one computer according to the fourth aspect; and the position tracking system for tracking the position of a physical object; and an augmented reality device having a distance measurement unit and an output unit display for outputting the augmentation information.

In general, the invention does not involve or for example comprise or encompass an invasive step which would represent a substantial physical interference with the body requiring professional medical expertise to be carried out and entailing a substantial health risk even when carried out with the required professional care and expertise. For example, the invention does not comprise a step of irradiating the anatomical body part and/or the patient's body with ionizing radiation so that it does not comprise any steps of therapy of the human or animal body, for example it does not comprise any step of therapy or surgery. More particularly, the invention does not involve or in particular comprise or encompass any surgical or therapeutic activity. The invention is instead directed as applicable to reading and processing data and operating or controlling a computer to execute a program which causes the computer to perform the data processing method according to the first aspect. For this reason alone, no surgical or therapeutic activity and in particular no surgical or therapeutic step is necessitated or implied by carrying out the invention.

It is within the scope of the present invention to combine one or more features of one or more embodiments or aspects of the invention in order to form a new embodiment wherever this is technically expedient and/or feasible. Specifically, a feature of one embodiment which has the same or a similar function to another feature of another embodiment can be exchanged with said other feature, and a feature of one embodiment which adds an additional function to another embodiment can for example be added to said other embodiment.

Definitions

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively, or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia. The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

In an example, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The atlas data comprises positional information which can be matched (for example by applying an elastic or rigid image fusion algorithm) for example to positional information contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows to determine the relative position in up to three rotational dimensions and up to three translational dimensions from a single two-dimensional image.

The position of a marker device can be ascertained, for example by a medical navigation system. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained once or twice or more over time.

A navigation system (within this disclosure also called position tracking system), such as a surgical navigation system, is understood to mean a system which can comprise: at least one marker device (such as the above-mentioned infrared-reflecting marker device or electromagnetic marker device); a transmitter which emits electromagnetic waves and/or radiation and/or ultrasound waves onto the at least one marker device; a receiver (such as the above-identified multi-dimensional position detector, for example the infrared-sensitive stereotactic camera or array of resonant coil circuits) which receives electromagnetic waves and/or radiation and/or ultrasound waves from the at least one marker device; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand. The position of the at least one marker device can be determined by the data processing device from the electromagnetic waves and/or radiation and/or ultrasound waves received by the receiver.

DESCRIPTION OF THE FIGURES

In the following, the invention is described with reference to the appended figures which represent a specific embodiment of the invention. The scope of the invention is however not limited to the specific features disclosed in the context of the figures, wherein

FIG. 1 shows the basic flow of the method according to the first aspect, which starts with a step S11 of determining the pre-registration, followed by a step S12 of determining the position of the fine registration region 8. In subsequent step S13, the augmentation information is displayed.

FIG. 2 illustrates a flow of a specific embodiment of the algorithm shown in FIG. 1. In step S21, the augmentation system (augmented reality device 4) uses its distance measurement unit (depth sensor) to identify a body volume corresponding to an anatomical body part or a tracking markers (marker device) or other physical object 6 by measuring a distance between the distance measurement unit and the body volume or the tracking markers or other physical object 6, respectively. The result is obtained in step S22 as the position of the body volume or the tracking markers (a marker device) or other physical object 6, respectively, in a virtual coordinate space (coordinate system) associated with the augmented reality device 5. Steps S23 and S24 may be executed subsequently, before or in parallel to (simultaneously with) steps S21 and S22. Step S23 encompasses position tracking (identification) of the tracking markers by a tracking device embodying the position detector 4 of the position tracking system 2. The result of the tracking is obtained in step S24 as a position of the tracking markers in a virtual coordinate space associated with the position tracking system 2, namely the tracking coordinate system. In step S25, the two virtual coordinate spaces are registered with one another (i.e. the spatial relationship, in particular transformation of bases between the two coordinate spaces is determined, for example by point-based rigid registration).

In subsequent step S26, the position of the tracking device is determined in the coordinate system associated with the augmented reality device 5. In step S27, the field of view of the tracking system 2 is matched to the three-dimensional depth image (generated by the distance measurement using the distance measurement unit of the augmented reality device 5) to identify a physical area visible to the tracking system (i.e. to identify the field of view of the position tracking system 2 in the real image acquired by the augmented reality device 5). In step S28, this match is used to display information (the augmentation information) in the augmented reality device (also called augmentation device or augmentation system) 5, for example on instruments required for a certain registration method, with augmentation information and automatically determine the registration method to be used. In step S29, areas where the registration method for conducting the fine registration should be applied are determined and displayed as additional augmentation information on the display of the augmented reality device 5. While the fine registration is performed, the progress of the fine registration is displayed as augmentation information by highlighting visually the part of the fine registration region which has already been registered with the tracking coordinate system. In subsequent step S211, an estimated registration accuracy can be display as even further additional augmentation information.

Figure 3:
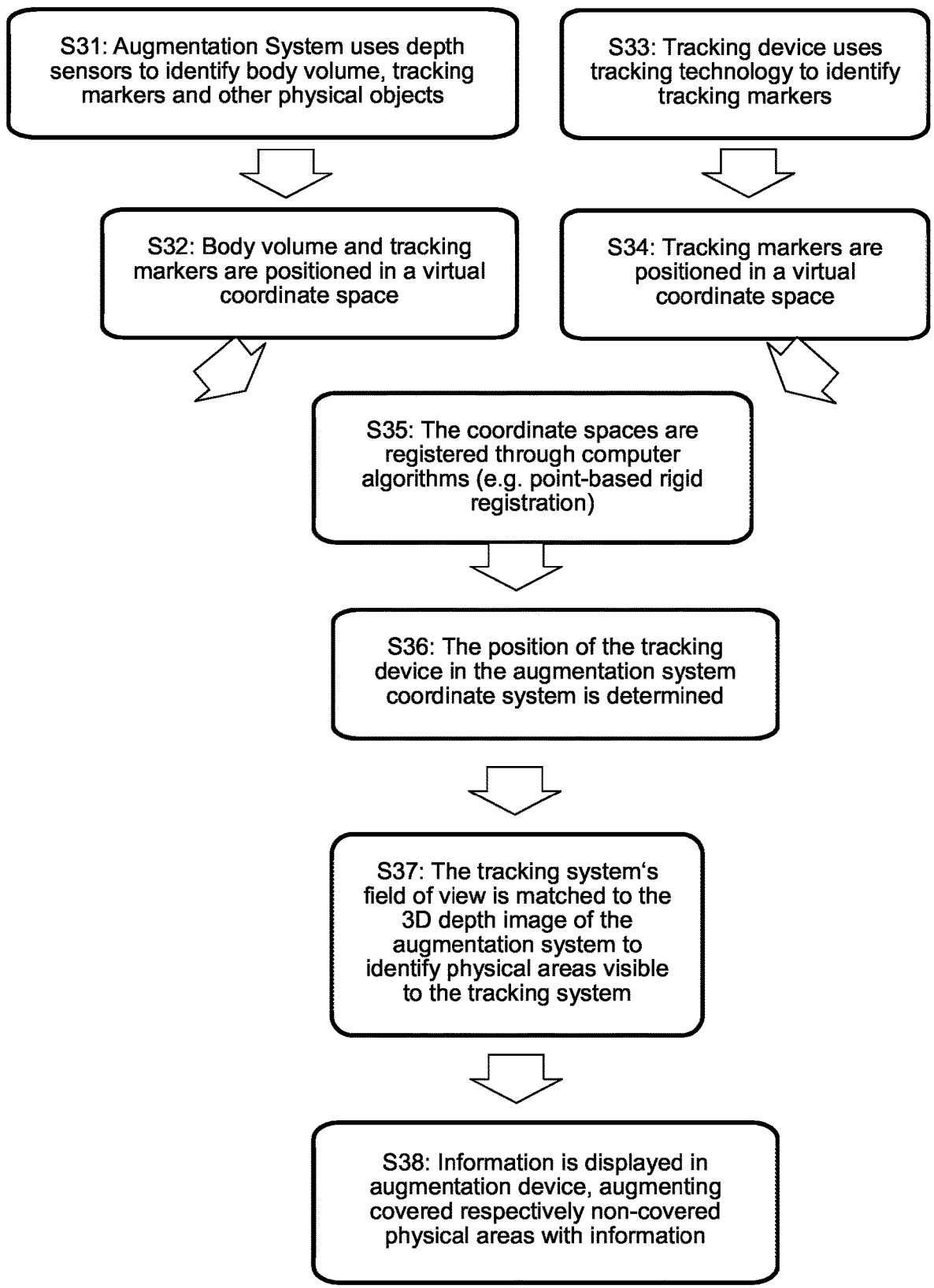
FIG. 3, FIG. 4, FIG. 5, and FIG. 6 illustrate four examples of generating the augmented reality device registration.

FIG. 3 illustrates a first example of determining the augmented reality device registration. In step S31, the augmentation system (augmented reality device 4) uses its distance measurement unit (depth sensor) to identify a body volume corresponding to an anatomical body part or a tracking markers (marker device) or other physical object 6 by measuring a distance between the distance measurement unit and the body volume or the tracking markers or other physical object 6, respectively. The result is obtained in step S32 as the position of the body volume or the tracking markers (a marker device) or other physical object 6, respectively, in a virtual coordinate space (coordinate system) associated with the augmented reality device 5. Steps S33 and S34 may be executed subsequently, before or in parallel to (simultaneously with) steps S31 and S32. Step S31 encompasses position tracking (identification) of the tracking markers by a tracking device embodying the position detector 4 of the position tracking system 2. The result of the tracking is obtained in step S34 as a position of the tracking markers in a virtual coordinate space associated with the position tracking system 2, namely the tracking coordinate system. In step S35, the two virtual coordinate spaces are registered with one another (i.e. the spatial relationship, in particular transformation of bases between the two coordinate spaces is determined, for example by point-based rigid registration).

In subsequent step S36, the position of the tracking device is determined in the coordinate system associated with the augmented reality device 5. In step S37, the field of view of the tracking system 2 is matched to the three-dimensional depth image (generated by the distance measurement using the distance measurement unit of the augmented reality device 5) to identify a physical area visible to the tracking system (i.e. to identify the field of view of the position tracking system 2 in the real image acquired by the augmented reality device 5). In step S38, this match is used to display information (the augmentation information) in the augmented reality device (also called augmentation device or augmentation system) 5, for example to augment areas in the real image covered or non-covered, respectively, by the field of view of the tracking system 2, with augmentation information.

Figure 1:
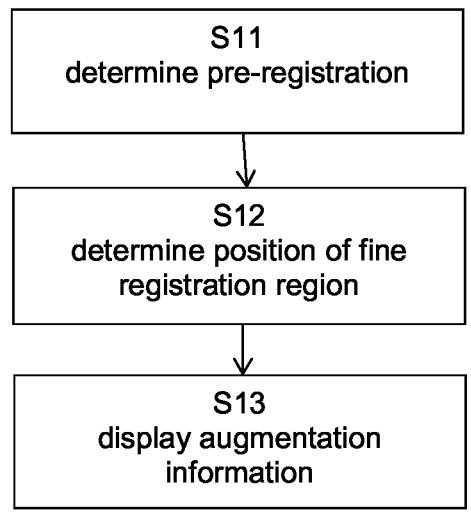
FIG. 1 is a flow diagram illustrating the basic steps of the method according to the first aspect.
Figure 2:
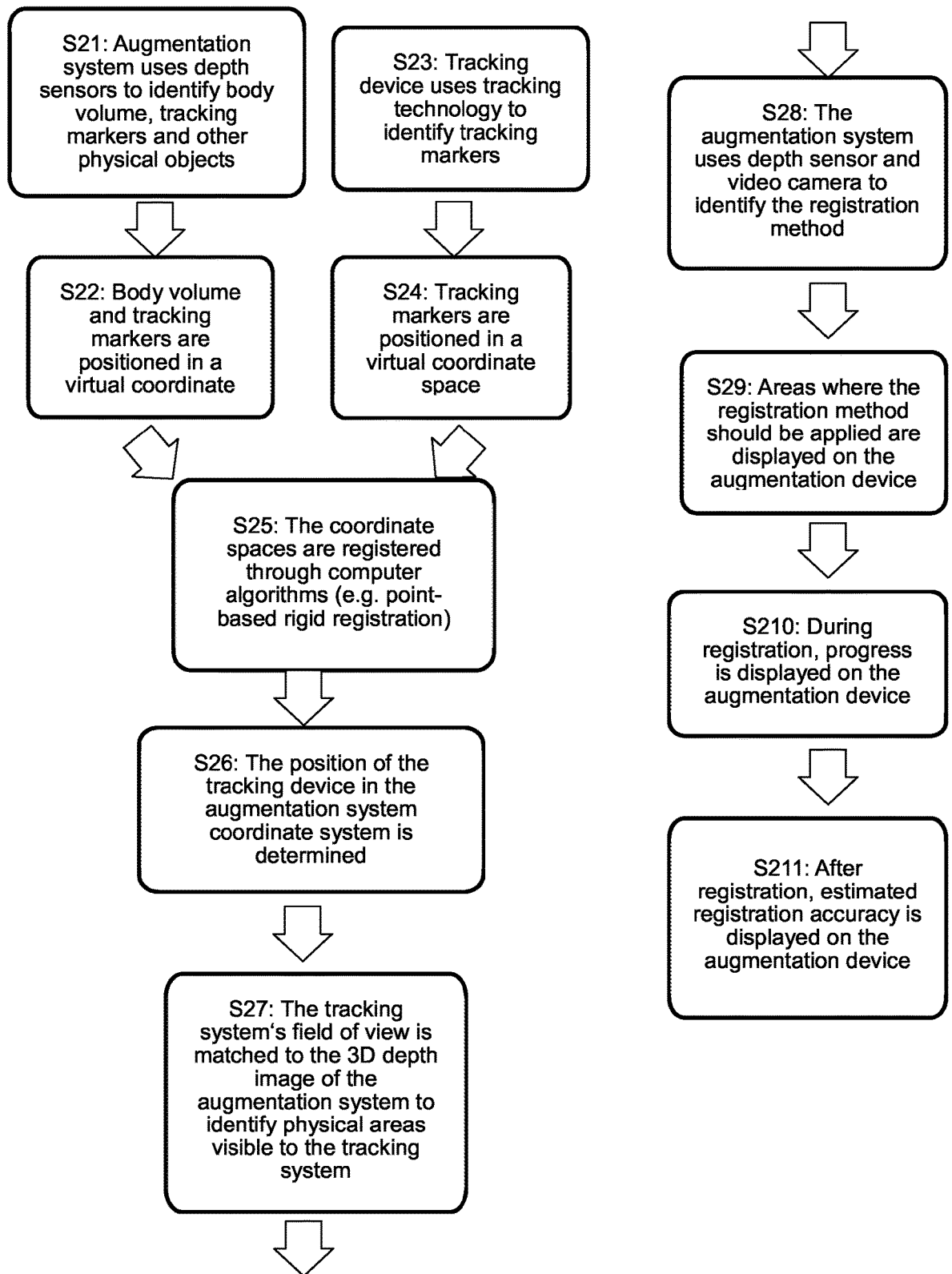
FIG. 2 illustrates a specific variant of the algorithm of FIG. 1.
Figure 4:
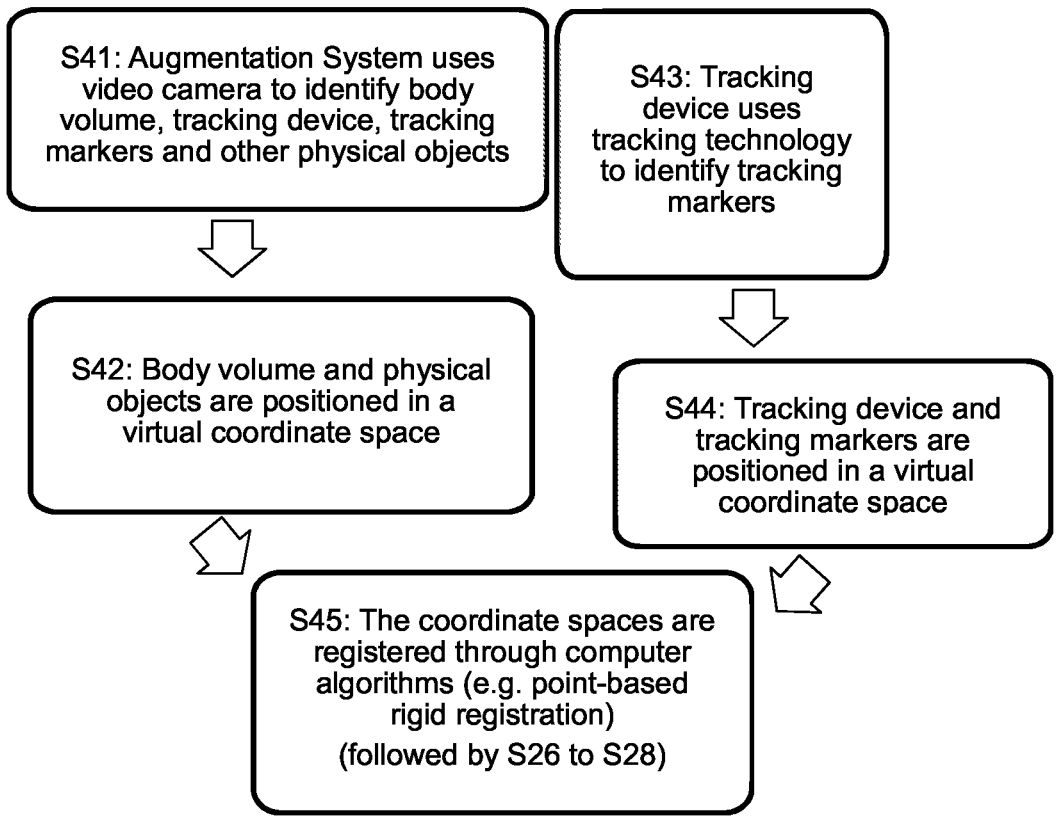

FIG. 4 shows a variation of the example of FIG. 3 in which step S41 encompasses the augmented reality device 5 using a video camera to identify a body volume, a tracking device, a marker device (tracking marker) or another physical object 6. Subsequently, the position of the body volume and the physical object is determined in a virtual coordinate space associated with the augmented reality device 5. Steps S43 and S44 may be executed before, after or in parallel to (i.e. simultaneously with) steps S41 and S42. Steps S43 and S44 correspond to steps S33 and S34, respectively, of FIG. 2. Subsequent step S45 corresponds to step S35 of FIG. 2, and is followed by steps S36 to S38 of FIG. 2.

Figure 5:
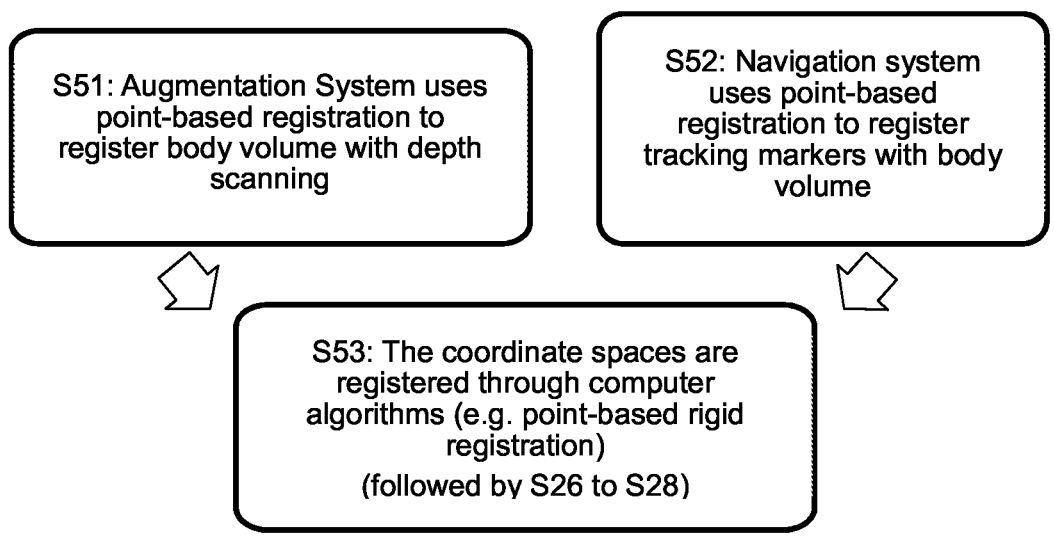

FIG. 5 shows a further variation of the example of FIG. 3 in which step S51 encompasses the augmented reality device 5 using point-based registration to register a body volume by depth scanning (i.e. surface scanning using the distance measurement unit of the augmented reality device 5). Step S52 may be executed before, after or in parallel to (i.e. simultaneously with) step S51. Subsequent step S53 corresponds to step S35 of FIG. 2, and is followed by steps S36 to S38 of FIG. 2.

Figure 6:
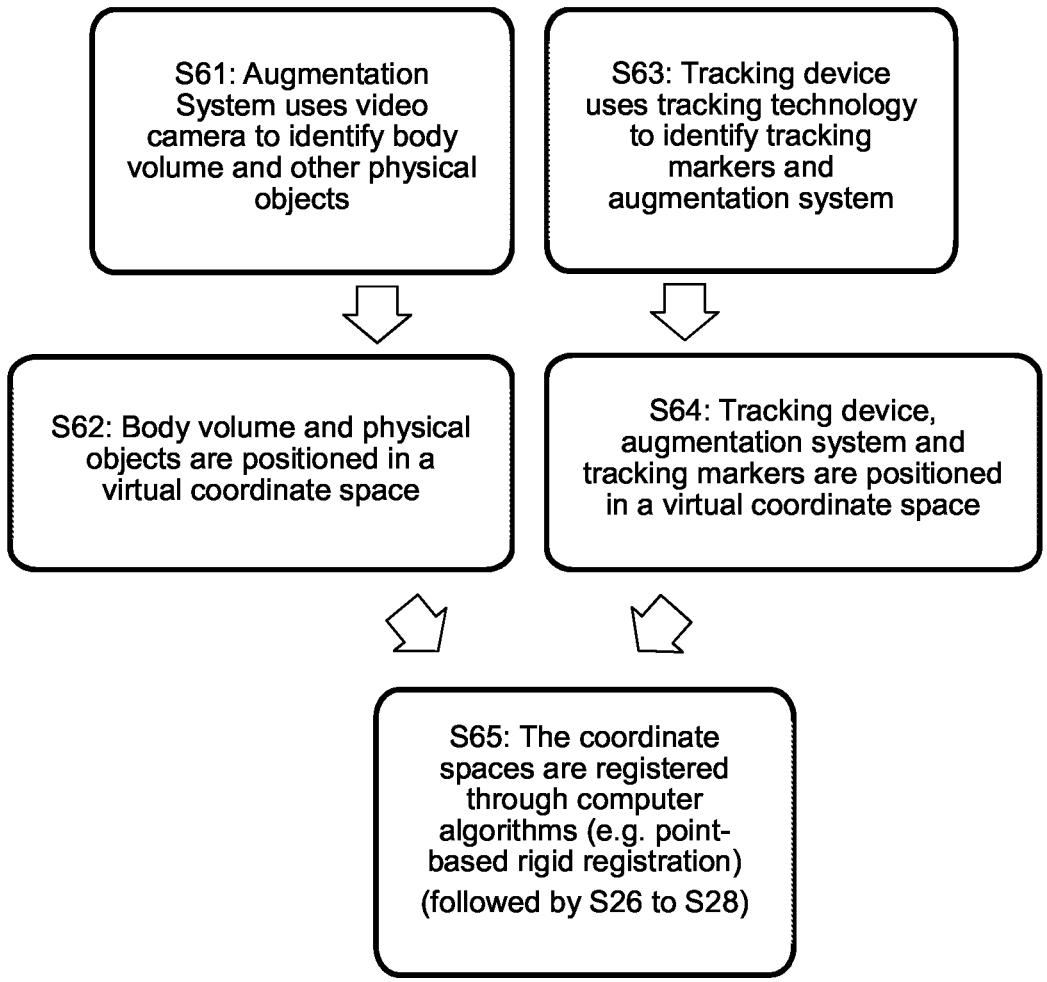

FIG. 6 shows a combination of an even further variation of the example of FIG. 3 with a variation of the example of FIG. 3 in which steps S61 and S62 correspond to steps S31 and S32, respectively. S66 encompasses the augmented reality device 5 using point-based registration to register a body volume by depth scanning (i.e. surface scanning using the distance measurement unit of the augmented reality device). Steps S63 and S64 may be executed before, after or in parallel to (i.e. simultaneously with) steps S61 and S62. In step S63, the position tracking system 2 identifies both the marker device and the augmentation system (by applying the respective tracking technology). The result of step S63 is determined in step S64 by determining the position of the marker device and the position of the augmented reality device 5 in step S64 in a virtual coordinate space associated with the position tracking system 2 (the tracking coordinate system). Subsequent step S63 corresponds to step S35 of FIG. 3, and is followed by steps S36 to S38 of FIG. 3.

Figure 7:
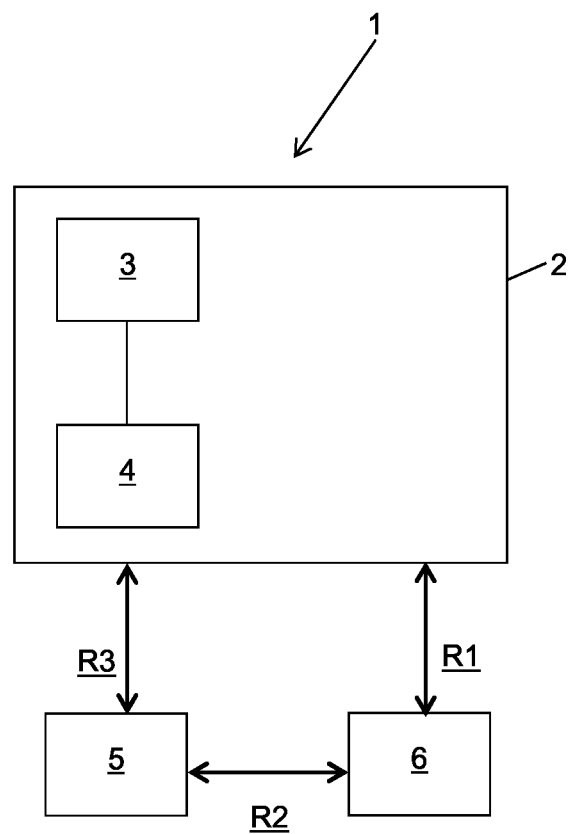
FIG. 7 illustrates the setup of the medical system according to the sixth aspect.

FIG. 7 gives a schematic overview of the medical system 1 according to the sixth aspect. The medical system 1 comprises a position tracking system 2 which comprises a computer 3 which is operably coupled to a multi-dimensional position detector 4. The augmented reality device 5 and optionally a physical object 6 are also part of the medical system 1. Within the framework of this disclosure, examples are given for determining a registration (relative position) R1 between the position tracking system 2 and the physical object 6, a registration (relative position) R2 between the physical object 6, and a registration (relative position) R3 between the augmented reality device 5 and the position tracking system 2.

Figure 8:
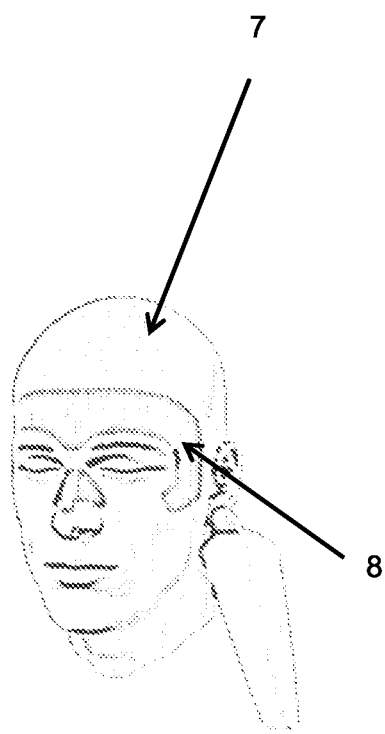
FIG. 8 illustrates a first example of the augmentation information.

FIG. 8 shows an example of augmentation in a view from the augmented glasses (i.e. in the real image). On the anatomical body part 7 embodied by the forehead, an area is displayed within the glasses where the registration process should be performed. That area constitutes the fine registration region 8. As registration is performed in the fine registration region 8, the registered part of the fine registration region 8 changes its colour or other appearance feature to indicate that registration should be performed on other parts of the fine registration region 8.

Figure 9:
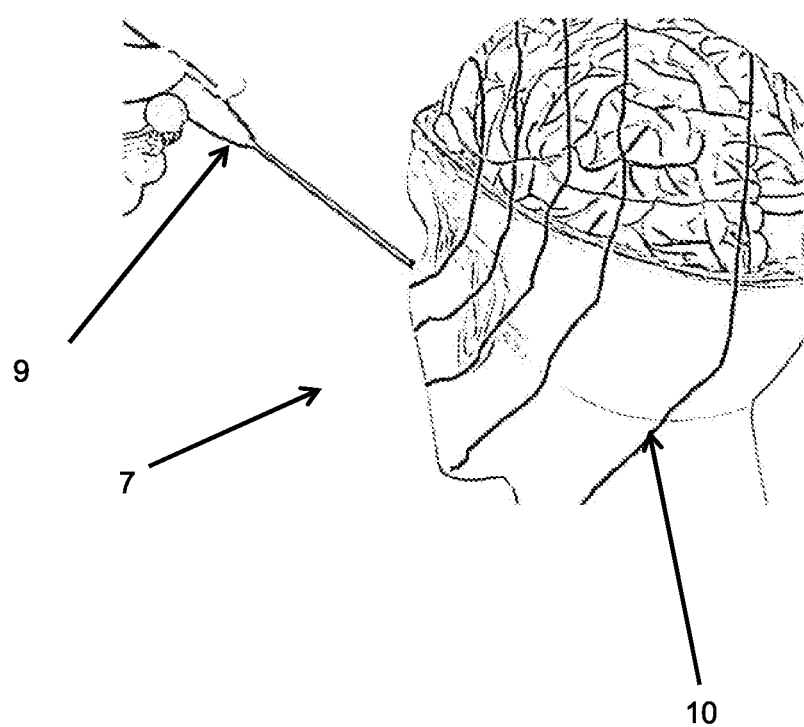
FIG. 9 illustrates a second example of the augmentation information.

FIG. 9 illustrates a variant of the augmentation information which in this example includes isolines 10 displayed on the anatomical body part 7 embodied by patient's head. The isolines 10 represent a measure of accuracy for detecting, by the tracking system 2, the position of points in the fine registration region 8 identified by using a tracked pointing device 9.

The method according to the first aspect may be summarized as follows:

First, a correspondence of the coordinate systems of the tracking device and the augmentation system needs to be determined.

One of the following methods (or a combination thereof) may be applied:

The augmentation system identifies a tracking marker (assembly) through the use of video cameras The augmentation system identifies a body volume via depth sensors that is registered to tracking markers The augmentation system identifies a volume via depth sensors that is also picked by depth sensors contained in the tracking system The augmentation system possesses tracking markers itself The augmentation system identifies the tracking device itself through video cameras or depth sensors.

The next step—the registration procedure—is intended to provide a correspondence between the coordinate system of the tracking device and the coordinate system of the patient imaging. During the registration procedure, the information generated by combining the coordinate systems of the tracking device and the augmentation system can be used to define a rough preregistration. This can be done through one of the methods above either in isolation or in combination with a rough body volume identification through one of the devices.

Based on the established correspondence, otherwise invisible aspects related to the tracking device can be augmented to the user's view by converting virtual objects from the tracking device into the augmentation coordinate system.

This can further comprise mapping this information on to a surface picked up by the depth sensors or determining the shadow area of objects depicted by the depth sensors of the augmentation system which might be invisible by the tracking device.

The correspondence between the two coordinate systems enables the registration process to be performed quicker through the rough pre-registration with depth field tracking and increased feedback and guiding information displayed directly on the augmentation device's image of the patient.

The tracking device may be an infra-red tracking device (usable in surgery or radiotherapy), an E/M (electromagnetic) tracking device, articulated arm or any other tracking device. The augmentation device could be any device with the ability to use another tracking method from a different direction. The second device incorporates a display, e.g. a head-mounted display in glasses worn by the user.

To improve surgical navigation or patient positioning in radiotherapy, the following can be calculated and displayed on the augmented reality device, specifically in augmented reality glasses:

Areas or points where the user should apply the selected registration method are displayed within the augmented reality device overlaid on the patient image. This could e.g. be areas that the surgeon needs to scan/identify with a pointing device (e.g. Z-touch, a product and registered trademark of Brainlab AG).

In combination with the previously acquired indication and anatomical mapping, the region where registration should be applied (e.g. certain spine vertebra) could be visualized within the augmented device.

The progress of the registration method is displayed on the overlays on the patient image. These can include marking of areas/points either registered or not yet registered. It can also include a general progress indicator.

During registration, the areas of the patient where surgical navigation or radiation therapy positioning can be applied with the currently calculated accuracy are displayed. This can be areas indicated by isolines with a specific accuracy.

During registration, areas on the patient that are required for registration but currently not in the field of view of the registration tracking device are visualized within the augmentation device.

Instructions on how to apply the selected registration method are displayed within the augmentation device.

The registration method chosen by the user could be determined automatically by using the depth sensor and visual sensor (camera) of the augmentation device to determine the registration device (pointing device) applied by the user.

The invention claimed is:

1. A computer-implemented method for pre-registering an anatomical body part of a patient's body, using output of an augmented reality device having a distance measurement unit, the method comprising executing, on at least one processor of at least one computer, the following steps:
    determining a pre-registration of the anatomical body part being the result of determining a position of the anatomical body part in an augmented reality coordinate system associated with the augmented reality device based on the result of a distance measurement by the distance measurement unit,
    wherein the augmented reality coordinate system is a coordinate system in which positional values of augmentation information are defined for display by the augmented reality device,
    wherein the augmented reality device comprises a display included in glasses wearable by a user and the distance measurement unit is positioned on the glasses;
    acquiring, based on a distance measurement by the distance measurement unit, surface detection data which describes a surface geometry of a marker device tracked by a medical position tracking system;
    acquiring marker device template data which describes a geometrical template of the marker device;
    determining a relative position between the augmented reality device and the anatomical body part based on the surface detection data and the marker device template data;
    positionally registering a viewing direction of the augmented reality device with a tracking coordinate system based on the determined relative position between the augmented reality device and the marker device,
    wherein at least one of the pre-registration or the position of a fine registration region is determined based on the registration of the viewing direction;
    determining, based on the pre-registration, the position of the fine registration region of the anatomical body part in a real image acquired by the augmented reality device,
    wherein the fine registration region is an area which serves as an area for fine registration with the tracking coordinate system of the medical position tracking system using a pointing tool tracked by the medical position tracking system for identifying at least one point in the fine registration region to the medical position tracking system; and
    outputting, by the augmented reality device, augmentation information describing the position of the fine registration region.

2. The method according to claim 1 wherein the augmentation information is displayed on a display of the augmented reality device or projected into an eye of a user by a projector unit of the augmented reality device.

3. The method according to claim 1 wherein the distance measurement unit has at least one light source for emitting measurement light onto a physical object.

4. The method according to claim 3 wherein the distance measurement unit has at least one detecting unit for detecting reflections of the measurement light from the physical object.

5. The method according to claim 1 wherein the augmentation information describes at least one of the following:

at least one surface area or at least one point on the anatomical body part which has to be positionally identified for the fine registration region;

at least one surface area or at least one point on the anatomical body part which has to be positionally identified for the fine registration region but is not within the field of view of the medical position tracking system usable to conduct the fine registration region;

at least one part of the fine registration region which has already been identified to the medical position tracking system by using a pointing device for conducting the fine registration region;

at least one visual indication describing a region associated with a determined accuracy of the positional tracking by the medical position tracking system;

at least one instruction to a user how to apply a previously selected method for conducting the fine registration region; and at least one region which shall not be positionally identified for the fine registration region.

6. The method according to claim 1 wherein the augmentation information is displayed as an overlay onto the real image.

7. The method according to claim 1 wherein
the medical position tracking system is an infra-red position tracking system and wherein a marker device is an infrared-reflective marker device which has a predetermined position relative to the fine registration region for allowing tracking of the anatomical body part by the medical position tracking system, or wherein the medical position tracking system is an electromagnetic position tracking system and the marker device is an electromagnetic marker device which has a predetermined position relative to the fine registration region for allowing tracking of the anatomical body part by the medical position tracking system.

8. The method according to claim 1 wherein the augmented reality device is tracked by the medical position tracking system.

9. The method of claim 8 wherein an infrared-reflective marker device or an electromagnetic marker device is attached to the augmented reality device.

10. The method of claim 8 wherein the viewing direction of the augmented reality device is positionally registered with the tracking coordinate system based on the result of tracking the augmented reality device.

11. The method according to claim 1 wherein the medical position tracking system has a distance measurement unit, and wherein the method comprises the following steps:
acquiring surface detection tracking data which describes a surface geometry of the anatomical body part based on a distance measurement by the distance measurement unit of the medical position tracking system; and
positionally registering the viewing direction of the augmented reality device with the tracking coordinate system based on the surface detection data and the surface detection tracking data; and
based on distance measurements by the distance measurement unit of the medical position tracking system and the distance measurement unit of the augmented reality device, wherein
at least one of the pre-registration or the position of the fine registration region is determined based on the registration of the viewing direction.

12. The method according to claim 1 wherein the augmented reality device comprises an image acquisition unit for acquiring a video image or still image, and wherein the method further comprises:
acquiring tracking system surface template data which describes a geometrical template of at least part of the medical position tracking system;
obtaining an image describing the at least part of the medical position tracking system from the image acquisition unit; and
positionally registering the viewing direction of the augmented reality device with the tracking coordinate system based on the tracking system surface template data and the image describing the medical position tracking system, wherein
at least one of the pre-registration or the position of the fine registration region is determined based on the registration of the viewing direction.

13. The method according to claim 1 wherein the method comprises the following steps:
acquiring tracking system surface template data which describes a geometrical template of at least part of the medical position tracking system;
acquiring tracking system surface detection data which describes a surface geometry of the at least part of the medical position tracking system based on a distance measurement by the distance measurement unit of the augmented reality device; and
wherein the viewing direction of the augmented reality device is positionally registered with the tracking coordinate system based on the tracking system surface template data and the tracking system surface detection data, and
wherein at least one of the pre-registration or the position of the fine registration region is determined based on the registration of the viewing direction.

14. The method according to claim 1 wherein the augmented reality device comprises a visible image acquisition unit for acquiring a video image or still image in a visible wavelength range, wherein the method further comprising:
acquiring code pattern template data which describes a template of a code pattern attached to at least part of the medical position tracking system;
obtaining a code pattern image describing the code pattern attached to the at least part of the medical position tracking system from an image acquisition unit; and
positionally registering the viewing direction of the augmented reality device with the tracking coordinate system based on the code pattern template data and the code pattern image, wherein
at least one of the pre-registration or the position of the fine registration region is determined based on the registration of the viewing direction.

15. The method according to claim 1 wherein the position of the fine registration region is determined based on generating a three-dimensional scene using distance measurements by the distance measurement unit of the augmented reality device.

16. The method according to claim 15 wherein the pre-registration is to be used for comparison with a full registration.

17. A system for determining augmentation information relating to positional tracking by a medical position tracking system, the system comprising:
at least one computer having at least one processor with associated memory, the memory storing instructions causing the at least one processor to:

determine a pre-registration of an anatomical body part being the result of determining a position of the anatomical body part in an augmented reality coordinate system associated with an augmented reality device based on the result of a distance measurement by a distance measurement unit;
wherein the augmented reality device comprises a display included in glasses wearable by a user and the distance measurement unit is positioned on the glasses;
wherein the augmented reality coordinate system is a coordinate system in which positional values of augmentation information are defined for display by the augmented reality device;
acquiring, based on a distance measurement by the distance measurement unit, surface detection data which describes
a surface geometry of a marker device tracked by the medical position tracking system;
acquiring marker device template data which describes a geometrical template of the marker device;
determining a relative position between the augmented reality device and the anatomical body part based on the surface detection data and the marker device template data;
positionally registering a viewing direction of the augmented reality device with a tracking coordinate system based on the determined relative position between the augmented reality device and the marker device,
wherein at least one of the pre-registration or the position of a fine registration region is determined based on the registration of the viewing direction;
determining, based on the pre-registration, the position of the fine registration region of the anatomical body part in a real image acquired by the augmented reality device,
wherein the fine registration region is an area which serves as an area for fine registration with the tracking coordinate system of the medical position tracking system using a pointing tool tracked by the medical position tracking system for identifying at least one point in the fine registration region to the medical position tracking system; and
outputting, by the augmented reality device, augmentation information describing the position of the fine registration region.

* * * * *